US012076495B2

(12) United States Patent
Travers et al.

(10) Patent No.: US 12,076,495 B2
(45) Date of Patent: Sep. 3, 2024

(54) VISUAL DISORDER TREATMENT

(71) Applicant: Luminopia, Inc., Cambridge, MA (US)

(72) Inventors: Dean Travers, Cambridge, MA (US); Scott Xiao, Cambridge, MA (US); Alexander Wendland, Cambridge, MA (US)

(73) Assignee: Luminopia, Inc., Cambridge, MA (US)

( * ) Notice: Subject to any disclaimer, the term of this patent is extended or adjusted under 35 U.S.C. 154(b) by 444 days.

(21) Appl. No.: 16/420,557

(22) Filed: May 23, 2019

(65) Prior Publication Data

US 2019/0366031 A1 Dec. 5, 2019

Related U.S. Application Data

(60) Provisional application No. 62/675,233, filed on May 23, 2018.

(51) Int. Cl.
*A61M 21/02* (2006.01)
*A61B 3/113* (2006.01)
(Continued)

(52) U.S. Cl.
CPC ............ *A61M 21/02* (2013.01); *G06F 3/1423* (2013.01); *A61B 3/113* (2013.01);
(Continued)

(58) Field of Classification Search
CPC ............ A61M 21/02; A61M 2021/005; A61M 2209/088; A61M 2230/63;
(Continued)

(56) References Cited

U.S. PATENT DOCUMENTS 6,511,175 B2   1/2003   Hay et al.
7,033,025 B2   4/2006   Winterbotham
(Continued)

FOREIGN PATENT DOCUMENTS

CN   102048611 B   11/2012
CN   104603673 B    3/2017
(Continued)

OTHER PUBLICATIONS

Peter Ziak, Anders Holm, Juraj Halicka, Peter Mojzis, and David P Pinero, Amblyopia treatment of adults with dichoptic training using the virtual reality oculus rift head mounted display: preliminary results, BMC Opthalmology, Jun. 28, 2017, 105, 17(1).
(Continued)

*Primary Examiner* — Sunita Reddy
(74) *Attorney, Agent, or Firm* — Sterne, Kessler, Goldstein & Fox P.L.L.C.

(57) ABSTRACT

Methods and systems for maintaining user attention during a treatment are disclosed. The method comprises measuring at least one user parameter when presenting treatment content to the user via at least one display screen, determining whether the user is engaged with the presented treatment content based on the at least one measured user parameter, presenting an attention booster to the user upon determining the user is not engaged with the treatment content. The system comprises at least one display apparatus configured to present treatment content to the user and a processor configured to execute instructions stored on a memory to measure at least one user parameter when the treatment content is presented to the user, determine whether the user is engaged with the presented treatment content based on the at least one measured user parameter, and output to the display apparatus an attention booster to the user upon
(Continued)

determining the user is not engaged with the presented treatment content.

18 Claims, 3 Drawing Sheets

(51) Int. Cl.
*A61M 21/00* (2006.01)
*G06F 3/14* (2006.01)

(52) U.S. Cl.
CPC . *A61M 2021/005* (2013.01); *A61M 2209/088* (2013.01); *A61M 2230/63* (2013.01)

(58) Field of Classification Search
CPC .. A61M 2021/0016; A61M 2021/0022; A61M 2021/0027; A61M 2205/332; A61M 2205/3592; A61M 2205/505; A61M 2205/507; A61M 2210/06; A61M 2230/10; A61M 21/00; A61M 2210/0612; A61M 2230/04; A61M 2230/16; G06F 3/1423; A61B 3/113; A61B 3/0041; G09G 3/20; G09G 2354/00
USPC .................................................. 128/897–899
See application file for complete search history.

(56) References Cited

U.S. PATENT DOCUMENTS

| | | | |
|---|---|---|---|
| 8,066,372 B2 | 11/2011 | Cooperstock et al. | |
| 8,328,354 B2 | 12/2012 | Li et al. | |
| 8,770,750 B2 | 7/2014 | Vendel et al. | |
| 8,820,930 B2 | 9/2014 | Fateh | |
| 9,186,293 B2 | 11/2015 | Krenik | |
| 9,706,910 B1 | 7/2017 | Blaha et al. | |
| 2003/0214630 A1* | 11/2003 | Winterbotham | A61H 5/00 351/203 |
| 2006/0087618 A1 | 4/2006 | Smart et al. | |
| 2010/0073469 A1* | 3/2010 | Fateh | A61B 3/10 348/62 |
| 2010/0283969 A1* | 11/2010 | Cooperstock | A61B 3/032 351/201 |
| 2012/0069296 A1* | 3/2012 | Li | A61B 3/08 351/201 |
| 2012/0179076 A1 | 7/2012 | Bavelier et al. | |
| 2014/0370479 A1* | 12/2014 | Gazzaley | A61B 5/168 434/322 |
| 2015/0305964 A1* | 10/2015 | Vadai | A61B 3/08 601/37 |
| 2016/0026009 A1* | 1/2016 | Urbajs | A61F 9/04 349/13 |
| 2016/0184170 A1* | 6/2016 | Bunker | A61H 5/00 601/37 |
| 2017/0007115 A1 | 1/2017 | Samec et al. | |
| 2017/0281412 A1* | 10/2017 | Hess | A61F 9/022 |
| 2017/0340200 A1* | 11/2017 | Blaha | A61B 3/113 |
| 2017/0347874 A1* | 12/2017 | Novik | G06F 3/016 |
| 2018/0028777 A1* | 2/2018 | Cheng | A61B 5/4854 |
| 2018/0132751 A1* | 5/2018 | Yarden | A61B 5/7445 |
| 2019/0035293 A1* | 1/2019 | Mei | G06F 3/013 |
| 2019/0255350 A1* | 8/2019 | Malchano | A61B 5/377 |
| 2019/0290528 A1* | 9/2019 | Sgambelluri | A61H 5/00 |
| 2019/0320962 A1* | 10/2019 | Hill | A61B 5/163 |

FOREIGN PATENT DOCUMENTS

| | | |
|---|---|---|
| CN | 107224261 A | 10/2017 |
| DE | 102014014799 A1 | 4/2016 |
| WO | 2017053871 A2 | 3/2017 |

OTHER PUBLICATIONS

PE Waddingham, SV Cobb, RM Eastgate, and RM Gregson, Virtual reality for interactive binocular treatment of amblyopia, Virtual Reality & Assoc. Tech, Apr. 1, 2006, 155-62, 5(2), Freud Publishing House Limited.

Angelo Gargantini, Using Stereoscopic 3D Technologies for the Diagnosis and Treatment of Amblyopia in Children, Sep. 28, 2011.

* cited by examiner

VISUAL DISORDER TREATMENT

CROSS-REFERENCE TO RELATED APPLICATIONS

The present application claims the benefit of and priority to U.S. provisional application No. 62/675,233, filed on May 23, 2018, the entire disclosure of which is hereby incorporated by reference as if set forth in its entirety herein.

TECHNICAL FIELD

Embodiments of the present disclosure relate to ensuring attention during the passive treatment of disorders or during the viewing of media content, and, more particularly, to a system and method for determining whether a user is engaged with a presented content based on at least one measured user parameter and presenting an attention booster to the user upon determining the user is not engaging with the content.

BACKGROUND

Visual disorders are commonly treated by presenting some type of treatment content to a patient. Often times, however, the patient may become bored with the treatment content or otherwise stop paying attention to the treatment content. This is particularly true of young children. This may ultimately lead to the patient going untreated or not receiving the full benefit of treatment.

It is imperative that the user pays attention to the treatment content. Hence, there is a need for an improved system and method for monitoring, maintaining, and ensuring user attention when treatment content is presented to the user.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

In one aspect, embodiments relate to a method for maintaining user attention during a treatment. The method includes measuring at least one user parameter when presenting treatment content to the user via at least one display screen, determining whether the user is engaged with the presented treatment content based on the at least one measured user parameter, and presenting an attention booster to the user upon determining the user is not engaged with the treatment content.

In some embodiments, the attention booster is an interactive test to be completed by the user.

In some embodiments, the attention booster is pre-selected by the user.

In some embodiments, the user parameter is eye movement of the user.

In some embodiments, the at least one user parameter is measured continuously.

In some embodiments, the at least one user parameter is measured intermittently.

In some embodiments, the attention booster is configured to at least partially occlude an image displayed on the at least one display screen.

In another aspect, embodiments relate to a system for maintaining user attention during treatment. The embodiment includes at least one display apparatus configured to present treatment content to the user, and a processor configured to execute instructions stored on a memory to measure at least one user parameter when the treatment content is presented to the user, determine whether the user is engaged with the presented treatment content based on the at least one measured user parameter, and output to the display apparatus an attention booster to the user upon determining the user is not engaged with the presented treatment content.

In some embodiments, the attention booster is an interactive test to be completed by the user.

In some embodiments, the attention booster is pre-selected by the user.

In some embodiments, the user parameter is eye movement of the user.

In some embodiments, the at least one measured user parameter is measured continuously.

In some embodiments, the at least one measured user parameter is measured intermittently.

In some embodiments, the attention booster is configured to at least partially occlude an image displayed on the at least one display apparatus.

In some embodiments, the display apparatus comprises a first display screen aligned with a first eye of the user and a second display screen aligned with a second eye of the user.

In some embodiments, the display apparatus comprises at least one augmented reality lens.

In some embodiments, the display apparatus is configured to alter at least one of the brightness, blurring, contrast, resolution, timing of presentation of input, and spatial frequencies.

In some embodiments, the display apparatus is configured to present virtual objects to each eye of the user independently.

In some embodiments, the user parameter is assessed with at least one of a physical controller, motion data from head movements within a virtual reality headset, and physiological measurements.

In some embodiments, the attention booster comprises at least one of leveraging optokinetic nystagmus, implementing sideways grating stimuli ties, and flashing an area surrounding the video background in the virtual reality while simultaneously displaying a video to the user.

In another aspect, embodiments relate to a method for maintaining user attention during a treatment. The embodiment includes presenting treatment content to the user via at least one display screen and presenting an attention booster to the user at pre-selected time-based intervals.

BRIEF DESCRIPTION OF THE DRAWINGS

Non-limiting and non-exhaustive embodiments of this disclosure are described with reference to the following figures, wherein like reference numerals refer to like parts throughout the various views unless otherwise specified.

Figure 1:
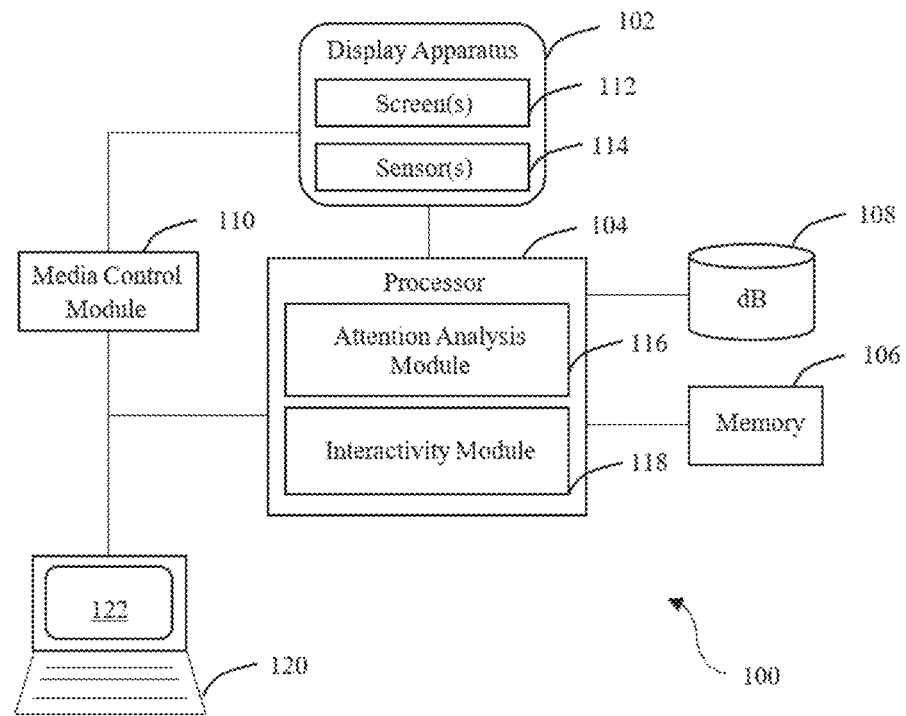
FIG. 1 illustrates a system for maintaining visual attention in accordance with one embodiment.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used. A variety of programming languages may be used to implement the present disclosure as discussed herein.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

The terms "comprises", "comprising", or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by "comprises . . . a" does not, without more constraints, preclude the existence of other devices, sub-systems, elements, structures, components, additional devices, additional sub-systems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

In accordance with various embodiments described herein, a display apparatus may display content (e.g., treatment content) to a user via one or more display screens. The systems and methods described herein may use various monitoring technologies (e.g., eye tracking, electroencephalogram monitoring, visual evoked potential monitoring, device accelerometer measurements, etc.) to gauge the user's visual attention continually or intermittently. Using these measurements, the systems and methods described herein may determine whether the user is engaged with a presented treatment content, including the attention level of the user, and alter the processing and/or presentation of visual content to encourage attention.

In some embodiments, treatment may include any product or system associated with the health of the user. In some embodiments, treatment may refer to a system designed to improve or maintain the health of a person or promote a healthy lifestyle.

Should the systems and methods described herein determine that the user is not engaged with a presented treatment content, the system may, for example, present a rapidly moving object within the image to one or both eyes to draw the user's attention to the object and therefore back to the treatment content. The display apparatus may also rapidly flicker some or all of the input to one or both of the user's eyes (e.g., have visual content rapidly alternate between two different visual appearance states at greater than 0.5 Hz).

Further, for users with amblyopia, the stronger eye is actively suppressing the weaker amblyopic eye. These aforementioned techniques and these "attention boosters" can be used to prevent this suppression of the weaker eye and therefore reteach an amblyopic user to properly utilize their amblyopic eye.

In order to measure this suppression, the system may present an image to one eye or the other while simultaneously examining user physiological data to determine whether or not the image was identified/seen by the user. For example, an evocative image (e.g., a frightening picture) may, if seen by a user, result in a substantially simultaneous measurable physiological change. In some embodiments, this can be a useful, objective mechanism to monitor suppression and attention without requiring any active involvement of the user. In some embodiments, the system may present an image on the screen visible to one or both eyes of the user and, by leveraging eye tracking technology, head tracking through device accelerometer data, or other means of measurement, determine whether the user altered their gaze to look at the presented image. In some embodiments, the system may present an image to one eye or both eyes together in this described fashion while simultaneously measuring physiological data or implementing eye tracking for the purpose of measuring attention in users with or without amblyopia.

It is also noted that the systems and methods described herein may operate without requiring any user parameter measurements in some embodiments. For example, these attention boosters may appear at predetermined time intervals to aid in ensuring user attention, irrespective of any user parameter measurements. In some embodiments, the predetermined time intervals may be once every five minutes. In some embodiments, the predetermined time intervals may be preset by a user.

FIG. 1 depicts a system 100 for ensuring visual attention in accordance with one embodiment. The system 100 may include a display apparatus 102, a processor 104, a memory 106, a database 108, and a media control module 110.

In some embodiments, the display apparatus 102 may feature a head-mounted housing that aligns the user's eyes with two lenses (which may be internal to the housing). The display apparatus 102 may also include one or two display screens 112 on which the user views visual content through the lenses of the display apparatus 102.

In various embodiments, the display apparatus 102 has one unitary display screen 112, portions of which constitute "display screens" for each of the user's eyes. For example, a divider may be disposed within the display apparatus 102 between the lenses so that each eye may only view its respective "display screen." In some embodiments, the fields of view of the lenses may also restrict each of the user's eyes to only view its respective display screen 112.

In some embodiments, the display apparatus 102 may feature two distinct display screens 112, one aligned with each lens (and thus with one of the user's eyes). Regardless, the display apparatus 102 may be configured to display different visual content to each eye, as various treatment plans or applications require.

In some embodiments, the display apparatus 102 may be utilized in "augmented reality" scenarios in which a view of the user's surroundings is displayed on or through the display screens 112. For example, in some embodiments, the display apparatus may include a front-facing camera that captures images of the surroundings that substantially correspond to what the user would view without wearing the display apparatus 102. In some embodiments, the front-facing camera may face the same direction as the eyes of the user. In some embodiments, the display screens 112 may be transparent or translucent, such that the display screens 112 may allow the user to view the surroundings through the screens 112. In some embodiments, the display screens 112 may also be utilized to display visual content overlaid on the user's view of the surroundings.

Some embodiments may use augmented reality and/or virtual reality technology. In some embodiments, augmented reality technology may be an interactive experience of a real-world environment where the objects that reside in the real-world are enhanced by computer-generated perceptual information, sometimes across multiple sensory modalities. In some embodiments, virtual reality technology may refer to a user experience taking place within a simulated and/or immersive environment.

In various embodiments of the invention, the display apparatus 102 may alter the brightness, blurring, contrast, resolution, modify or filter out certain spatial frequencies, timing of the presentation of input, and/or other visual quality or characteristic of the visual content or visual input perceptible either on the apparatuses screen or through augmented reality lenses based on where the user is looking. The apparatus 102 may also make the prior modifications to either some or all of the visual input/visual content visible to each eye.

A display apparatus 102 utilizing augmented reality lenses serves two main purposes. The display apparatus 102 may alter the visual appearance of part or all of the real world visible through the augmented reality lenses and may also be capable of projecting a virtual object (presented upon at least one of the screens embedded in both augmented reality lenses) as if it was visible to the user in the real world. The virtual objects presented in the real world can be of any sort of dynamically rendered pixels/visual content, such as described above (e.g. videos, augmented reality operating systems, etc.). In some embodiments, the display apparatus 102 can present the virtual objects such that part or all of the objects are visible to each eye independently (e.g. if the system 100 is presenting a train, then the wheels may be presented to the user's left eye and the carriage to the right eye). The visual appearance of part of all of the visual content displayed to each eye and augmented on the real world through the augmented reality lenses may also be adjustable in any way of contrast, brightness, spatial frequency, or other visual perceptible ways in some embodiments. For instance, in some embodiments, the display apparatus 102 could occlude the left half of the left lens and the right half of the right lens, thereby forcing the user to combine input from both eyes to see the complete image. As a further example, the display apparatus could present the wheels of an augmented car object to the user's left eye and the body of said object to the right eye. Thus, when viewed through both eyes, the user perceives a single car object.

In some embodiments, the display apparatus 102 may also modify any of the aforementioned visually perceptible elements of the either eye's rendered object. In some embodiments, the display apparatus 102 may make a perceived car's wheels much dimmer as seen by the user's left eye and may enhance the contrast of the car's body as seen by the user's right eye. In various embodiments, the system 100 may be able to continually or intermittently map and interpret the user's environment with camera or imaging technologies. In some embodiments, the system 100 may then use available image processing techniques in order to analyze the user's environment and determine which objects are present in said environment. From this, in some embodiments, the system 100 may intelligently apply visual modifications to the environment.

For example, as opposed to reducing the contrast to the left half of one of the augmented reality lenses, in some embodiments, the system 100 may reduce the contrast to one or both eyes of an actual television or a car that the system detects in the real world. Accordingly, the visual content and/or visual input treatment modifications may be applied to real world items in order to create dynamic treatments.

In some embodiments, if the user is reading, the system 100 may force the user to more heavily use their weaker amblyopic eye by heavily reducing their ability to see the text through their stronger eye, and may leave the rest of the stronger eye's input untouched. In some embodiments, this technique may be used as part of amblyopia treatment. The display apparatus 102 may be paired with an eye tracking camera or imaging system to not only intelligently map a user's environment but to continually or intermittently determine where in the environment the user is looking in some embodiments.

Within either a virtual reality headset or augmented reality headset, the system 100 may be able to determine where the user is looking and may modify the processing of the visual input in any of the above described ways to provide therapeutic benefits in some embodiments. In the case of amblyopia, for example, the system 100 could constantly block part of the image visible to the stronger eye wherever the user is looking or it could enhance the image to the weaker eye wherever it determines the user is looking.

As another example, the system 100 could remove high spatial frequencies from the visual input/content of the visual object of the user's focus. In various embodiments, the modifications of visual content within a virtual reality system may also be based on intelligent image processing and modify specific detected entities within the video. For instance, image processing could detect the presence of faces in the video content that is being presented, and these faces could then be dynamically blurred or have their contrast reduced heavily in the input visible to the user's stronger eye in the case of amblyopia.

Some embodiments of the system 100 may use augmented reality and/or virtual reality closed loop features with monitoring to measure user functioning. In addition to the above embodiments, the display apparatus 102 may have the ability to measure a user's visual or neurological functioning through any available method, such as visual acuity testing, eye tracking, electroencephalogram monitoring ("EEG monitoring"), or visual evoked potential monitoring ("VEP monitoring"). The display apparatus 102 may measure any element of visual or neurological functioning, such as, but not limited to, visual acuity, stereo acuity, fixation stability, or VEP strength. In some embodiments, this measuring may allow the display apparatus 102 to gauge the severity of the user's visual condition, such as the depth of their amblyopia, the user's response to the modification of visual input/visual stimuli, or any other measurable endpoint.

In some embodiments, the gathered information regarding the severity of the user's condition or the user's responses to treatment may then be used to alter the degree to which the visual input/visual content is modified/processed or how visual objects are presented through the augmented reality lenses or virtual reality screens. With regard to gauging the user's response to input, for example, should the display apparatus 102 detect that a user's amblyopic eye is more engaged at 20% contrast reduction as opposed to a 10% contrast reduction for an input for the strong eye, then the display apparatus 102 may then set the contrast to 20%.

In some embodiments, the systems and methods described herein may initially baseline users such as children at the beginning of a therapeutic session and then gauge how their physiological state changes over time. Additionally or alternatively, the systems and methods described herein may present evocative stimuli and measure the speed/intensity of the user's physiological response once exposed to the stimuli.

In various embodiments, these components 112 and 114 of the display apparatus 102 may be assembled into a unitary headset. In some embodiments, the display apparatus 102 may feature a housing adapted to be worn by the user and contain the lenses through which the user views the visual content. The housing may feature an attachment mechanism, e.g., a slot and/or one or more clamps and/or posts, configured to receive and secure a mobile device to the housing such that the screen (or "display") of the mobile device is viewable through the lenses by the user. As used herein, the term "mobile device" refers to a mobile phone or tablet capable of executing locally stored applications and supporting wireless bi-directional communication and data transfer via the Internet or the public telecommunications infrastructure. Mobile devices include, for example, IPHONES (available from Apple Inc., Cupertino, California), BLACKBERRIES (available from RIM, Waterloo, Ontario, Canada), or any mobile phones equipped with the ANDROID platform (available from Google Inc., Mountain View, California); tablets, such as the IPAD and KINDLE FIRE; and personal digital assistants (PDAs). The bi-directional communication and data transfer can take place via, for example, one or more of cellular telecommunication, a wired connection, a Wi-Fi LAN, a point-to-point Bluetooth connection, and/or an NFC communication.

The processor 104 may be any suitable hardware device executing instructions stored on memory 106 using an appropriate programming language to achieve the analytical functions described above. Illustratively, the programming language used may include assembly language, Ada, APL, Basic, C, C++, Objective-C, Swift, C*, COBOL, dBase, Forth, FORTRAN, Java, Modula-2, Pascal, Prolog, Python, REXX, and/or JavaScript for example. Further, it is not necessary that a single type of instruction or programming language be utilized in conjunction with the operation of embodiments of the present invention. Rather, any number of different programming languages may be utilized as is necessary or desirable.

The processor 104 may include or otherwise execute an attention analysis module 116 and an interactivity module 118. The attention analysis module 116 may analyze the data received from the one or more sensors 114 to determine whether the user is paying attention to the treatment content presented on the display apparatus 102. If the attention analysis module 116 determines that, based on the received data, the user is not paying attention to the treatment content, the interactivity module 118 may cause the media control module 110 to present one or more attention boosters via the display apparatus 102.

For example, it has been shown that certain images draw visual attention more assuredly than others. These may include images of, for example, a snake or other evocative images. Accordingly, images such as these could be interleaved with visual content and/or input in order to more effectively draw the user's attention.

In some embodiments, an attention booster may comprise a visual display to a user. In some embodiments, an attention booster may be a sound or a vibration engineered to attempt to re-focus a user. In some embodiments, the attention booster may be any sensory booster, including any combination of sound, vision, smell, and/or touch stimuli. For example, in some embodiments, the attention booster may comprise playing a bird sound to a user via speakers in the display apparatus 102 and then prompting a user to identify the sound on the display apparatus 102. In some embodiments, the specific type of attention booster may be selected based on the selected user treatment.

The display apparatus 102 may also combine passive video playback within a virtual reality environment with active control, interactive elements that require user feedback. For example, while a video is playing in the display apparatus 102, an attention booster such as a mini game/interactive task may appear on the top of the video. The mini game/task may require the user to, for example, select five moving targets within the next ten seconds or else the video will stop playing.

Figure 2:
FIG. 2 presents an exemplary screenshot of a video with an attention boosting task in accordance with one embodiment.

For example, FIG. 2 presents an exemplary screenshot 200 of a video with a task. In this particular task, a cannon is presented to the user within a virtual environment. The user is tasked with actively moving the cannon by leveraging head movement in order to shoot "splats" at the video. No treatment is applied to the video of FIG. 2, but the concept holds similarly even when treatment is applied to the video.

The presented task need not be a task or game that can be objectively won or lost, but instead is actively controlled by the user. Furthermore, in some embodiments, the input mechanism for enabling the user to complete the task/game may include a physical controller, motion data from head movements within a virtual reality headset, other types of input means, or even physiological measurements such as HRV, EEG, pupil dilation, or other user parameters.

In some embodiments, the attention boosters may include any technique for increasing a user's visual attention. These may include those discussed above along with more subconscious techniques, such as leveraging optokinetic nystagmus, implementing sideways grating stimuli ties, or flashing the area surrounding the video background in the virtual reality while continuing to play the video. Any of these techniques, taken singularly or in combination, may be used.

Accordingly, the systems and methods described herein may leverage physiological feedback not as a therapeutic in itself but rather as an input mechanism to drive attention and engagement within the videos and environments presented by the display apparatus 102. For example, the interactive task may require a user to use a breathing technique to lower their heart rate in order to remove obstacles from in front of the video. As another example, the user may be tasked to remain at a certain level of autonomic arousal in order to modify the virtual environment within which a video is played.

As mentioned above, these attention boosters are not necessarily part of the treatment but instead serve different purposes. That is, the displayed video may comprise the treatment content, while the attention boosters ensure the user is focusing on the treatment content.

The features described above are not limited to treating disorders such as amblyopia, either. For example, the systems and methods described herein may be used for acute pain distraction as the immersive qualities of virtual reality may serve as a driving distraction from pain. The passive video viewing and attention boosters may drive engagement to ensure that the user is captivated during usage and remains engaged. The attention boosters used and the purposes of the attention boosters may vary and may depend on the application in certain embodiments.

In other words, within amblyopia specifically, the attention boosters may ensure that the user is viewing the treatment content actively. Within pain-related applications, the attention boosters distract the user from further sensations of pain by focusing attention on the content being presented within the system. These are only examples and the features of the systems and methods described herein may be implemented in any other applicable treatment setting.

In some embodiments, the system 100 may also include a platform for driving and creating the attention boosters. For example, the interactivity module 118 may allow an operator (e.g., a clinician) to create these attention boosters. Specifically, the interactivity module 118 may allow an operator to define specific parameters of the interactive elements and/or tasks during the presentation of the elements and/or tasks to the user or prior to the presentation of the elements and/or tasks to the user.

Accordingly, users may have a wide variety of attention boosters and other types of content from which to choose.

In accordance with various embodiments, the interactivity module 118 may instruct the media control module 110 to modify a source image to alter the content displayed by the display apparatus 102. For example, the media control module 110 may present a source image in an unmodified format within a virtual reality environment, and present objects (i.e., attention boosters) in front of the image to occlude parts of said image. These objects may move in front of the content and may be presented in such a way as to occlude complementary aspects of the video displayed to each eye.

An example of this may be having a visual object, such as a meteor, floating in front of the video over different aspects of each eye's view. This may help drive visual attention by constantly requiring the user to actively fuse the image beneath the moving object(s).

In some embodiments, the videos may have complementary moving occlusion portions that are partially or entirely occluding the video portions that are visible to each eye. Accordingly, these occlusions may force or otherwise encourage enhanced visual attention for the user to view the video fully.

As seen in FIG. 1, the system 100 may also include or otherwise be in communication with a user device 120 executing a user interface 122 in some embodiments. The user device 120 may allow a parent to have access to a web portal that allows the parent to select and curate content for another user, such as their child. The web portal may be in communication the media control module 110 and/or the processor 104, and may have access to a library of videos, content, and companion characters to select for the user. These libraries may be stored in the database 108 in some embodiments. This helps ensure attention through therapeutic usage by helping the user and family identify and curate the content that is most likely to be enjoyed by the user.

In some embodiments, a user may pre-select booster content to help determine whether the user is engaged with the treatment content. For example, the database 108 could include a series of questions associated with visual aids for the user to select as a future booster content to be implemented as part of the treatment content. By way of example, a parent could pre-select a visual pop-up of a ball and an associated prompt, asking the user to determine if the visual pop-up was a bear or a ball. The user would then be required to select the correct answer during treatment.

In addition to selecting content for the user, a parent may also review data regarding how well their child is engaging in or otherwise complying with treatment. For example, the parent may review this progress data using a web portal accessed via the user device 120.

Figure 3:
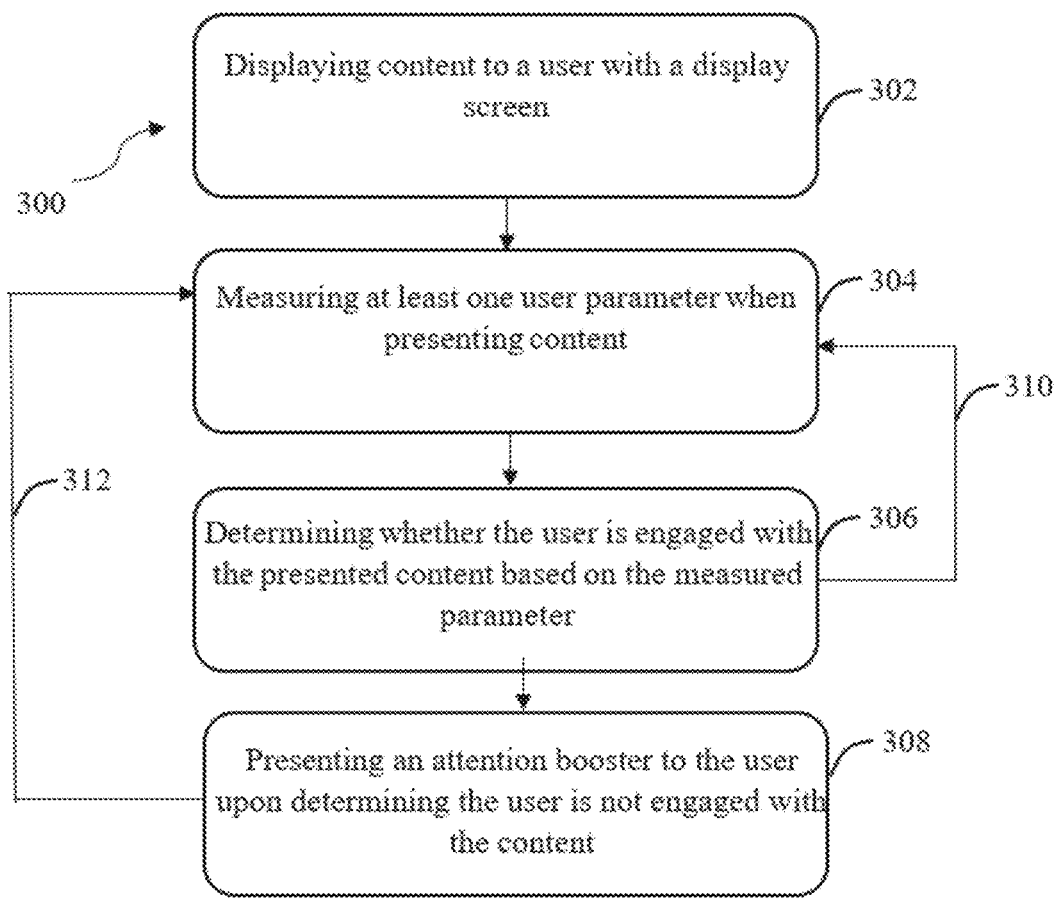
FIG. 3 depicts a flowchart of a method for maintaining user attention during treatment in accordance with one embodiment.

FIG. 3 depicts a flow chart 300 for maintaining user attention during treatment in accordance with some embodiments. As discussed above, in some embodiments, content is displayed to a user on a display screen 302. In some embodiments, the content is treatment content. When the user is watching the presented content, at least one parameter of the user may be measured 304. If the at least one parameter indicates that the user is not engaged with the presented content 306, an attention booster may be presented to the user 308. In some embodiments, after the attention booster is presented to the user, the at least one user parameter is then monitored again 312. In some embodiments, if the system determines that the user is engaging with the presented content 306, the system will not present an attention booster and will cycle back 310 to the previous step 304, continuing to measure the at least one user parameter. In some embodiments, the at least one user parameter 304 is measured continuously. In some embodiments, the at least one user parameter 304 is measured intermittently.

It will be understood by those skilled in the art that the foregoing general description and the following detailed description are exemplary and explanatory of the disclosure and are not intended to be restrictive thereof. While specific language has been used to describe the disclosure, any limitations arising on account of the same are not intended. As would be apparent to a person skilled in the art, various working modifications may be made to the method 150 in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

What is claimed is:

1. A method for maintaining user visual attention during a treatment of a visual disorder, the method comprising:
   presenting, by a processor, treatment content for the treatment of the disorder to a user via at least one display screen;
   measuring, by the processor, at least one user parameter while the treatment content is being presented to the user via the at least one display screen;
   determining, by the processor, that the user is not engaged with the treatment content based on the at least one measured user parameter; and
   presenting, by the processor, an attention booster to the user upon determining the user is not engaged with the treatment content to re-engage the user's attention on the treatment content,
   wherein the attention booster is independent from the treatment content in such a manner that the attention booster is not influenced by the treatment content; and
   wherein the attention booster comprises a visual object that is overlaid on the treatment content to at least partially occlude the treatment content.

2. The method of claim 1, wherein the presenting the attention booster comprises presenting an interactive activity to be completed by the user.

3. The method of claim 1, further comprising pre-selecting the attention booster by the user.

4. The method of claim 1, wherein the measuring comprises measuring eye movement of the user.

5. The method of claim 1, wherein the measuring comprises continuously measuring the at least one user parameter.

6. The method of claim 1, wherein the measuring comprises intermittently measuring the at least one user parameter.

7. A system for maintaining user visual attention during a treatment of a visual disorder, the system comprising:
   at least one display apparatus configured to present treatment content for the treatment of the disorder to a user; and
   a processor configured to execute instructions stored on a memory, the instructions, when executed by the processor, configuring the processor to:
   measure at least one user parameter while the treatment content is presented to the user;
   determine whether the user is engaged with the treatment content based on the at least one measured user parameter; and
   output to the at least one display apparatus an attention booster to the user upon determining the user is not engaged with the treatment content to re-engage the user's attention on the treatment content,
   wherein the attention booster is independent from the treatment content in such a manner that the attention booster is not influenced by the treatment content, and
   wherein the attention booster comprises a visual object that is overlaid on the treatment content to at least partially occlude the treatment content.

8. The system of claim 7, wherein the attention booster is an interactive test to be completed by the user.

9. The system of claim 7, wherein the attention booster is pre-selected by the user.

10. The system of claim 7, wherein the at least one user parameter is eye movement of the user.

11. The system of claim 7, wherein the instructions, when executed by the processor, configure the processor to continuously measure the at least one user parameter.

12. The system of claim 7, wherein the instructions, when executed by the processor, configure the processor to intermittently measure the at least one user parameter.

13. The system of claim 7, wherein the at least one display apparatus comprises a first display screen aligned with a first eye of the user and a second display screen aligned with a second eye of the user.

14. The system of claim 7, wherein the at least one display apparatus comprises at least one augmented reality lens.

15. The system of claim 7, wherein the at least one display apparatus is further configured to alter at least one of brightness, blurring, contrast, resolution, timing of presentation of input, and spatial frequencies.

16. The system of claim 7, wherein the at least one display apparatus is further configured to present virtual objects to each eye of the user independently.

17. The system of claim 7, wherein the at least one user parameter is assessed with at least one of a physical controller, motion data from head movements within a virtual reality headset, and physiological measurements.

18. A method for maintaining user visual attention during a treatment of a visual disorder, the method comprising:
  presenting, by a processor, treatment content for the treatment of the disorder to a user via at least one display screen; and
  presenting, by the processor, an attention booster to the user at time-based intervals to re-engage the user's attention on the treatment content based on the processor determining that the user is not engaged with the treatment content,
  wherein the attention booster is independent from the treatment content in such a manner that the attention booster is not influenced by the treatment content, and
  wherein the attention booster comprises a visual object that is overlaid on the treatment content to at least partially occlude the treatment content.

* * * * *